(12) United States Patent
Haag et al.

(10) Patent No.: US 12,350,647 B2
(45) Date of Patent: Jul. 8, 2025

(54) METHOD FOR PRODUCING SUPERABSORBENT PARTICLES

(71) Applicant: BASF SE, Ludwigshafen (DE)

(72) Inventors: Monica Haag, Ludwigshafen (DE); Stefan Gierescher, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 764 days.

(21) Appl. No.: 17/419,333

(22) PCT Filed: Jan. 13, 2020

(86) PCT No.: PCT/EP2020/050627
§ 371 (c)(1),
(2) Date: Jun. 29, 2021

(87) PCT Pub. No.: WO2020/151970
PCT Pub. Date: Jul. 30, 2020

(65) Prior Publication Data
US 2022/0080386 A1 Mar. 17, 2022

(30) Foreign Application Priority Data
Jan. 24, 2019 (EP) .................................. 19153439

(51) Int. Cl.
*B01J 20/26* (2006.01)
*A61L 15/22* (2006.01)
*A61L 15/24* (2006.01)
*A61L 15/42* (2006.01)
*A61L 15/60* (2006.01)
*B01J 20/28* (2006.01)
*B01J 20/30* (2006.01)

(52) U.S. Cl.
CPC ........... *B01J 20/267* (2013.01); *A61L 15/225* (2013.01); *A61L 15/24* (2013.01); *A61L 15/425* (2013.01); *A61L 15/60* (2013.01); *B01J 20/262* (2013.01); *B01J 20/28016* (2013.01); *B01J 20/3021* (2013.01); *B01J 20/3085* (2013.01)

(58) Field of Classification Search
None
See application file for complete search history.

(56) References Cited

U.S. PATENT DOCUMENTS

| | | | |
|---|---|---|---|
| 10,881,555 B2 | 1/2021 | Panayotova et al. | |
| 2006/0020049 A1* | 1/2006 | Champ | B01J 20/26 521/99 |
| 2008/0215026 A1 | 9/2008 | Schornick et al. | |
| 2016/0083532 A1 | 3/2016 | Wagner et al. | |
| 2019/0135993 A1 | 5/2019 | Daniel et al. | |

FOREIGN PATENT DOCUMENTS

| | | |
|---|---|---|
| DE | 102005011165 A1 | 9/2006 |
| DE | 102017205365 A1 | 10/2017 |
| EP | 3000486 A1 | 3/2016 |
| KR | 20190072298 A * | 6/2019 |
| WO | WO-2016/134905 A1 | 9/2016 |

OTHER PUBLICATIONS

International Application No. PCT/EP2020/050627, International Search Report, mailed May 19, 2020.
Graham, et al., "Chapter 3: Commercial Processes for the Manufacture of Superabsorbent Polymers", Modern Superabsorbent Polymer Technology, ed. Buchholz, et al., 2nd Edition, 1998, pp. 69-117.

* cited by examiner

Primary Examiner — Tanisha Diggs
(74) Attorney, Agent, or Firm — Element IP, PLC

(57) ABSTRACT

A process for producing superabsorbent particles, comprising polymerization of a monomer preparation, drying of the resultant aqueous polymer gel, grinding, classifying and thermal surface postcrosslinking, wherein the monomer preparation is produced by mixing an aqueous monomer solution and a foamed aqueous surfactant solution.

13 Claims, No Drawings

METHOD FOR PRODUCING SUPERABSORBENT PARTICLES

CROSS-REFERENCE TO RELATED APPLICATIONS

This is the U.S. national phase of International Application No. PCT/EP2020/050627, filed Jan. 13, 2020, which claims the benefit of European Patent Application No. 19153439.5, filed on Jan. 24, 2019.

The present invention relates to a process for producing superabsorbent particles, comprising polymerization of a monomer preparation, drying of the resultant aqueous polymer gel, grinding, classifying and thermal surface postcrosslinking, wherein the monomer preparation is produced by mixing an aqueous monomer solution and a foamed aqueous surfactant solution.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

To improve the performance properties, for example permeability (SFC) and absorption under a pressure of 49.2 g/cm$^2$ (AUHL), superabsorbent particles are generally surface postcrosslinked. This increases the level of crosslinking of the particle surface, which can at least partly decouple the absorption under a pressure of 49.2 g/cm$^2$ (AUHL) and the centrifuge retention capacity (CRC). This surface postcrosslinking can be performed in the aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the polymer particles.

EP 2 518 092 A1 describes the production of porous superabsorbent particles by foaming up the monomer solution prior to the polymerization.

It was an object of the present invention to provide an improved process for producing superabsorbent particles, especially for superabsorbent particles having higher liquid absorption.

The object was achieved by a process for producing superabsorbent particles, comprising polymerization of a monomer preparation, drying of the resultant aqueous polymer gel, grinding, classifying and thermal surface postcrosslinking, which comprises producing the monomer preparation by mixing an aqueous monomer solution comprising a) at least one ethylenically unsaturated monomer which bears acid groups and is at least partly neutralized,
b) at least one crosslinker and
c) at least one initiator, and a foamed aqueous surfactant solution.

In a preferred embodiment of the present invention, the polymerization of the monomer preparation is conducted in a kneading reactor. The aqueous monomer solution and the foamed aqueous surfactant solution are mixed here in the kneading reactor. The kneading reactor can be operated continuously or batchwise. A continuous kneading reactor is preferred.

Particularly suitable initiators c) are redox initiators. A redox initiator consists of an oxidizing component, for example sodium peroxodisulfate and/or hydrogen peroxide, and a reducing component, for example ascorbic acid. The reducing component is preferably not added until the kneading reactor.

The aqueous monomer solution comprises preferably from 30% to 60% by weight, more preferably from 35% to 65% by weight and most preferably from 40% to 50% by weight of the monomer a). The monomer a) has preferably been neutralized to an extent of from 40 to 90 mol %, more preferably from 50 to 85 mol %, most preferably from 60 to 80 mol %. The preferred monomer a) is partly neutralized acrylic acid.

The foamed aqueous surfactant solution comprises preferably from 0.1% to 10% by weight, more preferably from 0.5% to 5% by weight and most preferably from 1% to 3% by weight of at least one surfactant. The preferred surfactants are nonionic surfactants, for example ethoxylated 014-020 alcohols.

The surfactant solution is first foamed and only then is the already foamed surfactant solution mixed with the monomer solution.

The weight ratio of foamed aqueous surfactant solution to aqueous monomer solution in the monomer preparation is preferably from 0.01 to 0.30, more preferably from 0.02 to 0.20, most preferably from 0.03 to 0.10.

The present invention is based on the finding that the sequence of process steps has a crucial influence on the properties of the superabsorbent particles obtained. The inventive sequence of process steps, i.e. the mixing of an already foamed surfactant solution with a monomer solution, leads to a higher maximum temperature in the polymerization. Centrifuge retention capacity (CRC) and extractables of the base polymer are increased. After thermal surface postcrosslinking, the superabsorbent particles produced by the process of the invention have a distinctly improved volumetric liquid absorption under a pressure of 0.3 psi (2.07 kPa) (VAUL), a slight improvement in absorption under a pressure of 49.2 g/cm$^2$ (AUHL), and a comparable centrifuge retention capacity (CRC).

The foamed aqueous surfactant solution may additionally comprise a water-soluble polymer, preferably from 0.5% to 20% by weight, more preferably from 2% to 15% by weight and most preferably from 5% to 10% by weight. The preferred water-soluble polymers are polyethylene glycols.

There follows a detailed elucidation of the production of the superabsorbent particles:

The superabsorbent particles are produced by polymerizing a monomer solution and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

The monomers a) typically comprise polymerization inhibitors, preferably hydroquinone monoethers, as storage stabilizers.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized freeradically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

The amount of crosslinker b) is preferably 0.05% to 1.5% by weight, more preferably 0.1% to 1% by weight and most preferably 0.3% to 0.6% by weight, calculated in each case on the basis of the total amount of monomer a) used. With rising crosslinker content, centrifuge retention capacity (CRC) falls and the absorption under a pressure of 21.0 g/cm$^2$ (AUL) passes through a maximum.

Initiators c) used may be all compounds which generate free radicals under the polymerization conditions, for example thermal initiators, redox initiators or photoinitiators. Suitable redox initiators are sodium peroxodisulfate/ ascorbic acid, hydrogen peroxide/ascorbic acid, sodium peroxodisulfate/sodium bisulfite and hydrogen peroxide/ sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Typically, an aqueous monomer solution is used. The water content of the monomer solution is preferably from 40% to 70% by weight, more preferably from 45% to 65% by weight and most preferably from 50% to 60% by weight. It is also possible to use monomer suspensions, i.e. monomer solutions with monomer a) over and above the solubility, for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

The foamed surfactant solution comprises at least one surfactant. The at least one surfactant may be an anionic, cationic and/or nonionic surfactant. Nonionic surfactants are preferred, especially nonionic surfactants having an HLB value of 10 to 25. The HLB value is a measure of the water or oil solubility of predominantly nonionic surfactants and can be determined by customary methods.

A surfactant consists of at least one nonpolar group and at least one polar group. Preferred surfactants have large nonpolar and/or polar groups. Large groups are groups having a molar mass of at least 130 g/mol, preferably at least 250 g/mol, more preferably at least 500 g/mol.

Suitable surfactants are, for example, sorbitan esters, such as sorbitan monostearate, sorbitan monooleate, sorbitan monopalmitate and sorbitan monolaurate, and glycerol esters wherein the acid component derives from $C_{14}$ to $C_{20}$ carboxylic acids.

Preferred surfactants are alkoxylated, preferably ethoxylated, alcohols, where the alcohols may optionally be branched and/or unsaturated, and also alkoxylated, preferably ethoxylated, sorbitan mono esters such as sorbitan monostearate and sorbitan monooleate. Very particularly preferred surfactants are ethoxylated $C_{14}$-$C_{20}$ alcohols.

The at least one surfactant preferably has a viscosity of more than 20 mPas, more preferably of more than 25 mPas, most preferably of more than 30 mPas (measured at 23° C. to EN12092).

The foamed surfactant solution may additionally comprise water-soluble polymers. Water-soluble polymers used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably polyglycols such as polyethylene glycol.

The surfactant solution is foamed. All known methods of foaming are suitable for this purpose. The surfactant solution may, for example, be mixed vigorously with an inert gas, such as nitrogen or carbon dioxide.

The foamed surfactant solution is subsequently mixed and polymerized with the monomer solution. Since the foam has already been produced beforehand, there is no longer any need for vigorous mixing, for example rapid stirring.

Suitable reactors for the polymerization are, for example, kneading reactors or belt reactors. In the kneading reactor, the polymer gel formed in the polymerization of an aqueous monomer preparation is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted, for example in an extruder or kneading reactor.

To improve the drying properties, the comminuted polymer gel obtained by means of a kneading reactor can additionally be extruded.

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 40 to 90 mol %, more preferably from 50 to 85 mol % and most preferably from 60 to 80 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

The polymer gel is then typically dried with an air circulation belt drier until the residual moisture content is preferably 0.5 to 10% by weight, more preferably 1 to 7% by weight and most preferably 2 to 5% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 µm, more preferably from 250 to 600 µm, very particularly from 300 to 500 µm. The average particle size of the product fraction may be determined by means of EDANA recommended test method No. WSP 220.2 (05) "Particle Size Distribution", where the proportions by mass of the screen fractions are plotted in cumulative form and the average particle size is determined graphically. The average particle size here is the value of the mesh size which arises for a cumulative 50% by weight.

To further improve the properties, the polymer particles are thermally surface postcrosslinked. Suitable surface post-crosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

The amount of surface postcrosslinker is preferably 0.001% to 2% by weight, more preferably 0.02% to 1% by weight and most preferably 0.05% to 0.2% by weight, based in each case on the polymer particles.

In a preferred embodiment of the present invention, polyvalent cations are applied to the particle surface in addition to the surface postcrosslinkers.

The polyvalent cations usable in the process of the invention are, for example, divalent cations such as the cations of zinc, magnesium, calcium and strontium, trivalent cations such as the cations of aluminum, iron, chromium, rare earths and manganese, tetravalent cations such as the cations of titanium and zirconium. Possible counterions are chloride, bromide, hydroxide, sulfate, hydrogensulfate, carbonate, hydrogencarbonate, nitrate, phosphate, hydrogenphosphate, dihydrogenphosphate and carboxylate, such as acetate and lactate. Aluminum hydroxide, aluminum sulfate and aluminum lactate are preferred.

The amount of polyvalent cation used is, for example, 0.001% to 1.5% by weight, preferably 0.005% to 1% by weight and more preferably 0.02% to 0.8% by weight, based in each case on the polymer.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

The surface postcrosslinking is preferably performed in contact driers, more preferably shovel driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany), Holo-Flite® driers (Metso Minerals Industries Inc.; Danville; USA) and Nara Paddle Dryer (NARA Machinery Europe; Frechen; Germany). Moreover, fluidized bed driers may also be used.

The surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

Preferred reaction temperatures are in the range of 100 to 250° C., preferably 110 to 220° C., more preferably 120 to 210° C., most preferably 130 to 200° C. The preferred dwell time at this temperature is preferably at least 10 minutes, more preferably at least 20 minutes, most preferably at least 30 minutes, and typically at most 60 minutes.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 30 to 80° C., more preferably at 35 to 70° C., most preferably at 40 to 60° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in the cooler after the thermal surface postcrosslinking.

Suitable coatings for improving the free swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, precipitated silica, such as Sipernat® D17, and surfactants, such as Span® 20.

The present invention further provides the superabsorbent particles produced by the process of the invention.

The present invention further provides hygiene articles comprising superabsorbent particles produced by the process of the invention.

Methods:

The standard test methods described hereinafter and designated "WSP" are described in: "Standard Test Methods for the Nonwovens Industry", 2005 edition, published jointly by the Worldwide Strategic Partners EDANA (Herrmann-Debrouxlaan 46, 1160 Oudergem, Belgium, www.edana.org) and INDA (1100 Crescent Green, Suite 115, Cary, North Carolina 27518, USA, www.inda.org). This publication is obtainable both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Moisture Content

Moisture content is determined by EDANA recommended test method No. WSP 230.2 (05) "Mass Loss Upon Heating".

Centrifuge Retention Capacity

Centrifuge retention capacity (CRC) is determined by EDANA recommended test method No. WSP 241.2 (05) "Fluid Retention Capacity in Saline, After Centrifugation".

Absorption Under a Pressure of 21.0 g/Cm² (Absorption Under Load)

Absorption under a pressure of 21.0 g/cm² (AUL) is determined by EDANA recommended test method No. WSP 242.2 (05) "Absorption Under Pressure, Gravimetric Determination".

Absorption Under a Pressure of 49.2 g/Cm² (Absorption Under High Load)

Absorption under a pressure of 49.2 g/cm² (AUHL) is determined analogously to EDANA recommended test method No. WSP 242.2 (05) "Absorption Under Pressure, Gravimetric Determination", except that a pressure of 49.2 g/cm² (0.7 psi) is established rather than a pressure of 21.0 g/cm² (0.3 psi).

Extractables

The content of extractables in the superabsorbent particles is determined by EDANA recommended test method No. WSP 270.2 (05) "Extractable".

Surface Tension of the Aqueous Extract

To determine the surface tension of the aqueous extract (ST), 0.50 g of the superabsorbent particles is weighed into a small beaker and admixed with 40 ml of a 0.9% by weight salt solution. The contents of the beaker are stirred with a magnetic stirrer bar at 500 rpm for 3 minutes, then left to settle for 2 minutes. Finally, the surface tension of the supernatant aqueous phase is measured with a K10-ST digital tensiometer (Krüss GmbH; Hamburg, Germany) or comparable instrument with a platinum plate. The measurement is conducted at a temperature of 23° C.

Free Swell Rate

To determine the free swell rate (FSR), 1.00 g (=W1) of the superabsorbent particles is weighed into a 25 ml beaker and distributed homogeneously over its base. Then 20 ml of a 0.9% by weight sodium chloride solution are metered into a second beaker by means of a dispenser and the contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=W2). The time interval required for the absorption, which has been measured with the stopwatch, is designated as t. The disappearance of the last liquid droplet on the surface is determined as the time t.

The free swell rate (FSR) is calculated therefrom as follows:

$$FSR[g/gs]=W2/(W1 \times t)$$

If the moisture content of the superabsorbent particles, however, is more than 3% by weight, the weight W1 should be corrected to take account of this moisture content.

Permeability (Saline Flow Conductivity)

The permeability (SFC) of a swollen gel layer under a pressure of 0.3 psi (2070 Pa) is determined, as described in EP 2 535 698 A1, with a weight of 1.5 g of superabsorbent particles as a urine permeability measurement (UPM) of a swollen gel layer. The flow is detected automatically.

The permeability (SFC) is calculated as follows:

$$SFC[cm^3 s/g]=(Fg(t=0) \times L_0)/(d \times A \times WP)$$

where $Fg(t=0)$ is the flow of NaCl solution in g/s, which is obtained using linear regression analysis of the Fg(t) data of the flow determinations by extrapolation to t=0, $L_0$ is the thickness of the gel layer in cm, d is the density of the NaCl solution in g/cm³, A is the area of the gel layer in cm², and WP is the hydrostatic pressure over the gel layer in dynes/cm².

Volumetric Absorption of Liquid Under a Pressure of 0.3 Psi (2.07 kPa) (VAUL)

For the volumetric absorption of liquid under a pressure of 0.3 psi (2.07 kPa) (VAUL), the T value is determined by the test method "Volumetric Absorbency Under Load (VAUL)" described in WO 2014/079694 A1 on pages 39 and 40. The T value is described therein as the "characteristic swelling time".

EXAMPLES

Production of the Base Polymer

Example 1

A twin-shaft kneading reactor of the LUK 8.0K2 type (Coperion Werner & Pfleiderer GmbH & Co. KG, Stuttgart, Germany) was inertized by purging with nitrogen. The kneading reactor shafts were operated at 96 rpm and 48 rpm respectively. The shell of the kneading reactor was heatable by means of a heat transfer agent.

4901 g of a 37.3% by weight aqueous sodium acrylate solution and 571.9 g of acrylic acid were mixed, freed of oxygen by purging with nitrogen and introduced into the kneading reactor. Subsequently, a mixture of 7.9 g of triply ethoxylated glycerol triacrylate (about 85% strength by weight) and 100 g of acrylic acid, 11.89 g of aqueous sodium peroxodisulfate solution (about 15% strength by weight) and 132 g of aqueous hydrogen peroxide solution (about 3% strength by weight) were metered successively into the kneading reactor.

A surfactant solution of 250 g of water, 29.6 g of aqueous polyethylene glycol-4000 (about 50% strength by weight) and 9.9 g of 80-tuply ethoxylated 016/018 fatty alcohol (Lutensol® AT80) was foamed with nitrogen in a static mixer. Polyethylene glycol-4000 is a polyethylene glycol having an average molar mass of about 4000 g/mol. The resultant stable foam was then metered into the kneading reactor. The conduit was subsequently purged with about 200 g of water.

Subsequently, 19.7 g of aqueous ascorbic acid solution (about 0.5% strength by weight) was metered into the kneading reactor and the shell of the kneading reactor was heated by means of a heat transfer agent (80° C.). The temperature in the kneading reactor rose from 22° C. to 102° C. As soon as the rise in temperature had ended, the heating was switched off, the polymer gel obtained was kneaded for another 13 minutes, cooled to 63° C. and discharged from the kneading reactor.

The resultant polymer gel was distributed homogeneously on wire mesh trays in portions of about 1080 g and dried in an air circulation drying cabinet at 175° C. for 90 minutes. The resultant dried polymer gel was ground in three stages (1000 μm, 60 μm and 400 μm) with a roll mill of the LRC 250 type (Bauermeister Zerkleinerungstechnik GmbH, Norderstedt, Germany), and screened off to a particle size of 150 to 710 μm.

The superabsorbent particles obtained were analyzed. The results are collated in table 1.

Example 2

The procedure was as in example 1, except that the surfactant solution used was a solution of 250 g of water, 14.7 g of aqueous polyethylene glycol-4000 (about 50% strength by weight) and 4.9 g of 80-tuply ethoxylated $C_{16}/C_{18}$ fatty alcohol (Lutensol® AT80).

The superabsorbent particles obtained were analyzed. The results are collated in table 1.

Example 3 (Comparative Example)

The procedure was as in example 1, except without foaming.

The superabsorbent particles obtained were analyzed. The results are collated in table 1.

Example 4 (Comparative Example)

The procedure was as in example 1, except that a solution of 250 g of water and 29.6 g of aqueous polyethylene glycol-4000 (about 50% strength by weight) was used rather than the surfactant solution and there was no foaming.

The superabsorbent particles obtained were analyzed. The results are collated in table 1.

Example 5 (Comparative Example)

The procedure was as in example 1, except that a surfactant solution of 250 g of water and 9.9 g of 80-tuply ethoxylated 016/018 fatty alcohol (Lutensol® AT80) was used rather than the surfactant solution and there was no foaming.

The superabsorbent particles obtained were analyzed. The results are collated in table 1.

Example 6 (Comparative Example)

The procedure was as in example 1, except that the surfactant solution was metered into the monomer solution in the kneading reactor and it was only the mixture of monomer solution and surfactant solution in the kneading reactor that was foamed with nitrogen (1 bar, 1166 ml/min) with a cylindrical sintered filter element of the SIK-R 15 AX type (GKN Sinter Metal Filters GmbH, Radevormwald, Germany) for two minutes.

The superabsorbent particles obtained were analyzed. The results are collated in table 1.

TABLE 1

Properties of the base polymers

| Ex. | CRC [g/g] | AUL [g/g] | FSR [g/gs] | Ext. [% by wt.] | ST [mN/m] | $T_{max}$ [° C.] |
|---|---|---|---|---|---|---|
| 1 | 38.4 | 11.9 | 0.33 | 14.5 | 56.7 | 102 |
| 2 | 37.4 | 15.2 | 0.31 | 11.4 | 55.1 | 95 |
| 3*) | 35.9 | 18.7 | 0.31 | 7.9 | 54.1 | 89 |
| 4*) | 35.9 | 20.5 | 0.31 | 8.7 | 63.7 | 91 |
| 5*) | 34.5 | 23.2 | 0.34 | 8.6 | 54.7 | 93 |
| 6*) | 35.3 | 22.8 | 0.33 | 8.2 | 53.8 | 88 |

*)comparative example surface postcrosslinking

Example 7

1200 g of base polymer from example 1 were coated in a Pflugschar M5 plowshare mixer with heating jacket (Gebr. Lödige Maschinenbau GmbH; Paderborn, Germany) at 23° C. and a shaft speed of 200 revolutions per minute by means of a two-phase spray nozzle with 54.4 g of a mixture of 1.5% by weight of N-hydroxyethyl-2-oxazolidinone, 1.5% by weight of propane-1,3-diol, 26.7% by weight of isopropanol, 11.0% by weight of aluminum lactate and 59.3% by weight of water.

After the spray application, the shaft speed was reduced to 50 revolutions per minute and the product temperature was increased to 185° C. Subsequently, the reaction mixture was kept at this temperature and this shaft speed for 40 minutes. The resulting product was cooled to ambient temperature and classified again with a 710 μm sieve.

The superabsorbent particles obtained were analyzed. The results are collated in table 2.

Example 8

The procedure was as in example 7, except that the base polymer from example 2 was used. The superabsorbent particles obtained were analyzed. The results are collated in table 2.

Example 9 (Comparative Example)

The procedure was as in example 7, except that the base polymer from example 3 was used.

The superabsorbent particles obtained were analyzed. The results are collated in table 2.

Example 10 (Comparative Example)

The procedure was as in example 7, except that the base polymer from example 4 was used.

The superabsorbent particles obtained were analyzed. The results are collated in table 2.

Example 11 (Comparative Example)

The procedure was as in example 7, except that the base polymer from example 5 was used.

The superabsorbent particles obtained were analyzed. The results are collated in table 2.

Example 12 (Comparative Example)

The procedure was as in example 7, except that the base polymer from example 6 was used.

The superabsorbent particles obtained were analyzed. The results are collated in table 2.

TABLE 2

| | Properties after surface postcrosslinking | | | |
|---|---|---|---|---|
| Ex. | SFC $[10^{-7} cm^3 s/g]$ | CRC [g/g] | AUHL [g/g] | VAUL [s] |
| 7 | 35 | 30.0 | 27.4 | 162 |
| 8 | 33 | 31.0 | 27.6 | 196 |
| 9*) | 41 | 29.6 | 26.0 | 240 |
| 10*) | 39 | 29.1 | 26.2 | 232 |
| 11*) | 49 | 28.4 | 26.3 | 221 |
| 12*) | 47 | 30.0 | 26.5 | 254 |

*)comparative example

Comparison of examples 7 and 12 shows that the foaming of the surfactant solution in the absence of the monomer solution (example 7) leads to a distinctly different profile of properties than foaming in the presence of the monomer solution (example 12).

The invention claimed is:

1. A process for producing superabsorbent particles, comprising:
    foaming an aqueous surfactant solution to form a foamed aqueous surfactant solution;
    mixing the foamed aqueous surfactant solution with an aqueous monomer solution to obtain a monomer preparation, the aqueous monomer solution comprising:
        a) at least one ethylenically unsaturated monomer which bears an acid group and is at least partly neutralized,
        b) at least one crosslinker and
        c) at least one initiator; and
    polymerizing the monomer preparation, drying a resultant aqueous polymer gel, grinding, classifying and thermal surface postcrosslinking.

2. The process according to claim 1, wherein polymerizing of the monomer preparation is conducted in a kneading reactor and the aqueous monomer solution and the foamed aqueous surfactant solution are mixed in the kneading reactor.

3. The process according to claim 1, wherein the polymerizing is conducted in a continuous kneading reactor.

4. The process according to claim 1, wherein the aqueous monomer solution comprises from 40% to 50% by weight of the monomer a).

5. The process according to claim 1, wherein the monomer a) has been neutralized to an extent of 60 to 80 mol %.

6. The process according to claim 1, wherein the monomer a) is partly neutralized acrylic acid.

7. The process according to claim 1, wherein the foamed aqueous surfactant solution comprises from 1% to 3% by weight of at least one surfactant.

8. The process according to claim 1, wherein the foamed aqueous surfactant solution comprises at least one nonionic surfactant.

9. The process according to claim 1, wherein a weight ratio of the foamed aqueous surfactant solution to the aqueous monomer solution in the monomer preparation is from 0.03 to 0.10.

10. The process according to claim 1, wherein the foamed aqueous surfactant solution additionally comprises a water-soluble polymer.

11. The process according to claim 10, wherein the foamed aqueous surfactant solution comprises from 5% to 10% by weight of the additional water-soluble polymer.

12. The process according to claim 10, wherein the additional water-soluble polymer is polyethylene glycol.

13. The process according to claim 1, wherein the at least one initiator c) is a redox initiator.

* * * * *